(12) United States Patent
Gross et al.

(10) Patent No.: US 8,685,942 B2
(45) Date of Patent: Apr. 1, 2014

(54) SOPHOROLIPID ANALOG COMPOSITIONS

(76) Inventors: Richard A. Gross, Plainview, NY (US); Mark H. Schofield, New York, NY (US)

( * ) Notice: Subject to any disclaimer, the term of this patent is extended or adjusted under 35 U.S.C. 154(b) by 0 days.

(21) Appl. No.: 13/080,609

(22) Filed: Apr. 5, 2011

(65) Prior Publication Data

US 2012/0022241 A1 Jan. 26, 2012

Related U.S. Application Data

(60) Provisional application No. 61/320,885, filed on Apr. 5, 2010.

(51) Int. Cl.
*A61K 31/70* (2006.01)
*C07H 15/00* (2006.01)

(52) U.S. Cl.
USPC ........... 514/53; 536/17.9; 536/18.1; 536/18.2

(58) Field of Classification Search
None
See application file for complete search history.

(56) References Cited

PUBLICATIONS

Furstner et al., Journal of Organic chemistry, 2000, vol. 65, 8758-8762.*

* cited by examiner

*Primary Examiner* — Traviss C McIntosh, III
(74) *Attorney, Agent, or Firm* — Laurence P. Colton; Smith Risley Tempel Santos LLC

(57) ABSTRACT

A composition of matter comprising sophorolipids as antimicrobial agents, antifungal agents, biopesticides, for uses as drugs to treat HIV, septic shock, cancer, asthma, dermatological conditions, as spermicidal agents, as anti-inflammatory drugs, as ingredients in cosmetics and building blocks for monomers and polymers and self-assembled templates for further chemical elaboration.

3 Claims, 15 Drawing Sheets

$R^1$ = H, Ac
$R^2$ = H, Ac

| | |
|---|---|
| SL-A-1 | $R^1 = R^2 = Ac$ |
| SL-A-2 | $R^1 = Ac; R^2 = H$ |
| SL-A-3 | $R^1 = H; R^2 = Ac$ |
| SL-A-4 | $R^1 = R^2 = H$ |

| | |
|---|---|
| SL-E-1 | $R^1 = R^2 = H; R^3 = Me$ |
| SL-E-2 | $R^1 = R^2 = H; R^3 = Et$ |
| SL-E-3 | $R^1 = R^2 = H; R^3 = Bu$ |
| SL-E-4 | $R^1 = H; R^2 = Ac; R^3 = Et$ |
| SL-E-5 | $R^1 = R^2 = Ac; R^3 = Et$ |
| SL-E-6 | $R^1 = H; R^2 = Ac; R^3 = Bu$ |
| SL-E-7 | $R^1 = H; R^2 = Ac; R^3 = Bu$ |
| SL-E-8 | $R^1 = R^2 = Ac; R^3 = Bu$ |
| SL-E-9 | $R^1 = H; R^2 = H; R^3 = Hexyl$ |

X = H, OH, NH₂, NHR, SH, SR, OR; Y = H, OH, NH₂, NHR, SH, SR,
OR Z = O, NH, NR, S, CHR $R^1$ = H, Ac; $R^2$ = H, Ac

R³= H, alkyl, aryl, heterocyclic, cationic, anionic groups

E = (CH$_2$-CH$_2$O)$_n$H, CH$_2$-CH(OH)-CH$_2$NMe$_3^+$ or H$^+$

SOPHOROLIPID ANALOG COMPOSITIONS

BACKGROUND OF THE INVENTION

1. Technical Field

The present invention relates generally to the field of sophorolipids and more specifically to new compositions of matter for uses of sophorolipids as antimicrobial and antifungal agents; as biopesticides; for uses as drugs to treat HIV, septic shock, cancer, asthma, and dermatological conditions; as spermicidal agents; as anti-inflammatory drugs; as ingredients in cosmetics; as building blocks for monomers and polymers; and as self-assembled templates for further chemical elaboration.

2. Prior Art

Surfactants as cosmetics (neutral, anionic emulsifiers & surfactants); surfactants as antimicrobial and antifungal agents; surfactants as therapeutic agents.

Nature has evolved a class of compounds, known as sophorolipids that have antimicrobial properties. These natural biopesticides, which can be classified as microbial surfactants, are amphiphilic molecules produced by fermentation using substrates consisting of carbohydrates and lipids. Microbial biosurfactants are surface active compounds produced by various microorganisms. They lower surface and interfacial tension and form spherical micelles at and above their critical micelle concentration (CMC). Microbial biosurfactants generally have an amphiphilic structure, possessing a hydrophilic moiety, such as an amino acid, peptide, sugar or oligosaccharide, and a hydrophobic moiety including saturated or unsaturated lipid or fatty acids. Sophorolipids are produced by yeasts, such as *Candida bombicola* (see FIG. 1), *Yarrowi alipolytica, Candida apicola*, and *Candida bogoriensis*.

They consist of a hydrophilic carbohydrate head, sophorose, and a hydrophobic fatty acid tail with generally 16 or 18 carbon atoms. Sophorose is an unusual disaccharide that consists of two glucose molecules linked β-1,2. Furthermore, sophorose in sophorolipids can be acetylated on the 6'- and/or 6"-positions (FIG. 1). One fatty acid hydroxylated at the terminal or subterminal (ω-1) positions is β-glycosidically linked to the sophorose molecule. The fatty acid carboxylic acid group is either free (acidic or open form) or internally esterified generally at the 4"-position (lactonic form) (FIG. 1). The hydroxy fatty acid component of sophorolipids generally has 16 or 18 carbon atoms with generally one unsaturated bond (Asmer et al. 1988; Davila et al. 1993). However, the sophorolipid fatty acid can also be fully saturated. As such, sophorolipids synthesized by *C. bombicola* consist of a mixture of molecules that are related. Differences between these molecules are found based on the fatty acid structure (degree of unsaturation, chain length, and position of hydroxylation), existing in the lactonic or ring-opened form, and the acetylation pattern. Sophorolipids derivatives disclosed herein are described based on the predominant fatty acid constituent, 17-hydroxyoleic acid, produced by *C. bombicola* when fed crude oleic acid as its fatty acid source. However, because changes in the lipid feed lead to different sophorolipids as described above, variations in feedstock also will result in changes in composition of modified sophorolipid structures that are disclosed herein.

Work has been carried out to "tailor" sophorolipid (SL) structure during in vivo formation. These studies have mainly involved the selective feeding of different lipophilic substrates. For example, changing the co-substrate from sunflower to canola oil resulted in a large increase (50% to 73%) of the lactonic portion of SLs. See Zhou, Q.-H., et al., *J. Am. Oil Chem. Soc.* 1995, 72, 67; Zhou, Q.-H., et al., *J. Am. Oil Chem. Soc.* 1992; 69, 89; Asmer, H. J., et al., *J. Am. Oil; hem. Soc.* 1988, 65, 1460; Davila, A. M., et al., *Appl. Microbiol. Biotech.* 1992, 38, 6; Tulloch A. P., et al., *Can. J. Chem.* 1962, 40, 1326. Also, unsaturated C-18 fatty acids of oleic acid may be transferred unchanged into sophorolipids. Rau, U., et al., *Biotechnol. Lett.* 1996, 18, 149. Finally, lactonic and acidic sophorolipids are synthesized in vivo from stearic acid with similar yields to oleic acid-derived sophorolipids. Felse, P. A., et al., *Enzyme and Microbial Technology* 2007, 40 316-323. Thus, to date, physiological variables during fermentations have provided routes to the variation of sophorolipid compositions.

As noted above, fermentation by different microorganisms, *Candida bombicola, Yarrowi alipolytica, Candida apicola*, and *Candida bogoriensis*, leads to sophorolipids of different structure noted above, the variations in sophorolipids based on fatty acid feedstocks and organisms leads to a wide array of sophorolipids including lactonic and acidic structures. An additional modification that is relevant to the acidic sophorolipids is the cleavage of the sophorose to the corresponding glucose-based glucolipids. Treatment of acidic sophorolipids with enzymes β-Glucuronidase (*Helix pomatia*), Cellulase (*Penicillium funiculosum*), Clara diastasea, Galactomannanase (*Aspergillus niger*), Hemicellulase (*Aspergillus niger*), Hesperidinase (*Aspergillus niger*), Inulinase (*Aspergillus niger*), Pectolyase (*Aspergillus japonicus*), or Naringinase (*Penicillium decumbens*) afford glucolipids over a range of pH values. Rau, U., et al., *Biotechnology Letters* 1999, 21, 973-977).

The chain length of the fatty acid carbon source fed can result in changes in the predominant fatty acid incorporated into the sophorolipid produced. For example, Davila et al. (1994) found that when hexadecane and octadecane were fed in fermentations, over 70% of the hydroxylated fatty acids found in sophorolipids were hexadecanoic and octadecanoic acids, respectively. When shorter alkanes such as tetradecane are fed as substrates in fermentations, only a minor fraction of the sophorolipids produced by the organism consist of the corresponding hydroxylated shorter chain fatty acid. Instead, the vast majority of these shorter chain fatty acids are elongated to either C16 or C18 fatty acids. Similarly, when longer alkanes such as eicosane (C20) are fed to the sophorolipid producing organism, generally longer chain fatty acids are metabolized via β-oxidation to shorter chain length hydroxylated C16 and C18 fatty acids.

Furthermore, the degree of lactonization of sophorolipids and acetylation of the sophorose polar head may be influenced by the carbon source used. For example, Davila et al. (1994) claims that sophorolipids produced from oils are formed with higher levels of diacetylated lactones than sophorolipids produced from the corresponding fatty acid ester feedstocks. Davila A. M., et al., Sophorose lipid production from lipidic precursors-Predictive evaluation of industrial substrates. J. Ind. Microbiol. 13:249-257 (1994).

It is known that by modification of sophorolipids, their physical properties can be manipulated (Zhang et al., 2004). Modifications of SLs were performed so that the chain length of the n-alkyl group (methyl, ethyl, propyl, butyl, hexyl) esterified to the sophorolipid fatty acid was varied. The effect of the n-alkyl ester chain length on interfacial properties of corresponding sophorolipid analogues was studied (FIG. 2).

The cmc and minimum surface tension have an inverse relationship with the alkyl ester chain length. That is, cmc decreased to ½ per additional $CH_2$ group for the methyl, ethyl, and propyl series of chain lengths. These results were confirmed by fluorescence spectroscopy. Adsorption of sophorolipid alkyl esters on hydrophilic solids was also studied to explore the type of lateral associations. These surfactants were found to absorb on alumina but much less on silica. This adsorption behavior on hydrophilic solids is similar to that of sugar-based nonionic surfactants and unlike that of nonionic ethoxylated surfactants. Hydrogen bonding is proposed to be the primary driving force for adsorption of the sophorolipids on alumina. Increase in the n-alkyl ester chain length of sophorolipids caused a shift of the adsorption isotherms to lower concentrations. The magnitude of the shift corresponds to the change in cmc of these surfactants (FIG. 2). This study suggests that by careful modulation of sophorolipid structure via simple chemical modification, dramatic shifts in their surface-activity can be achieved to 'tune' their properties for a desired interfacial challenges. Furthermore, changes in interfacial properties are expected to relate to changes in biological properties.

Prior art describes limited ways in which sophorolipids can be modified for use as building blocks for polymer synthesis. For example, a mixture of sophorolipids produced by *Torulopsis bombicola* was esterified by reaction with sodium salts of n-alkanols. Using Novozym 435 as catalyst, the SL methyl ester, in the absence of acylating agent or with the acylating agent at a concentration less than equimolar, gave sophorolactone (Bisht et al, 1999). Spectral analysis of this compound showed that a synthetic analogue of microbially produced macrolactone was formed. Sophorolactone differs from the natural sophorolipid lactone in that the fatty acid carboxyl carbon is linked to the C-6 hydroxyl, not to the C-4 hydroxyl (FIG. 20). Subsequent acrylation of the new non-natural lactonic form of SL, catalyzed by Novozym 435, led to formation of the C-6 monoacryl derivative (Bisht et al, 2000). See FIG. 20.

The translation of complexity from natural sophorolipid building blocks to polymers was explored. In one example, a component of the natural sophorolipid mixture was used as a monomer for polymer synthesis. Specifically, lactonic sophorolipids, derived from fermentation of *Candida bombicola*, were polymerized by ring-opening metathesis polymerization (ROMP) catalysis. Poly(sophorolipid), poly(SL), was prepared in yield and $M_n$ up to 89% and 103 000, respectively (FIG. 3). By this chemo-biocatalytic route, unique polymers with disaccharide, ester, and monounsaturated hydrocarbon moieties were prepared. The unique poly(SL) structure consists of C18 oleic-like aliphatic segments (90% cis-configured double bonds) that alternate with bulky diacetylated disaccharide moieties (Zini et al., 2008). Solid-state properties were investigated using TGA, DSC, TMDSC, and variable-temperature X-ray diffraction. Poly(SL) is a solid at room temperature that undergoes a glass transition at 61° C. and melts at 123° C. The crystal phase is associated with ordered packing of aliphatic chain segments. Semicrystalline poly (SL) also displays a long-range order (d=2.44 nm) involving sophorose groups that is found to persist after crystal phase melting (in high-T diffractograms) with a slightly shortened distance (2.27 nm). Upon annealing at 80° C., poly(SL) recrystallizes and, concomitantly, the disaccharide units space out again at 2.44 nm. An exothermal phenomenon that immediately follows melting and is revealed by TMDSC might be associated with the observed adjustment of sophorose units spacing in the melt. See FIG. 3.

Various sophorolipid (SL) structures can be used to create self-assembled scaffolds that can serve as templates for further chemical elaboration. For example, non-acetylated acidic sophorolipids are bola amphiphiles with unique structures that include an asymmetrical polar head size (disaccharide vs. COOH), a kinked hydrophobic core (cis-9-octadecenoic chain), and a non-amide polar-nonpolar linkage (Zhou et al, 2004). Light microscopy, small- and wide-angle X-ray scattering, FT-IR spectroscopy, and dynamic laser light scattering were used to investigate supramolecular structures of SL self-assembled aggregates at different pH values. In acidic conditions (pH<5.5), giant twisted and helical ribbons of 5-11 μm width and several hundreds of micrometers length were observed for the first time (FIG. 4). By increasing the solution pH, ribbon formation slowed, decreased in yield, increased in helicity and entanglements of the giant ribbons. An interdigitated lamellar packing model of acidic SL-COOH molecules with a long period of 2.78 nm, stabilized by both the strong hydrophobic association between cis-9-octadecenoic chains and strong disaccharide-disaccharide hydrogen bonding was proposed (FIG. 5). New sophorolipid structures will be useful to manipulate the tendency to self assemble as well as the range of useful structures formed.

Various sophorolipid-based structures have been found useful as therapeutic agents. Experimental studies in mice and rats were performed to assess effects of sophorolipids on sepsis-related mortality when administered as a (1) single bolus versus sequential dosing and (2) natural mixture versus individual derivatives compared with vehicle alone (Bluth et al., 2006; Hardin et al., 2007). Intra-abdominal sepsis was induced in male, Sprague Dawley rats, 200 to 240 g, via cecal ligation and puncture. Sophorolipids (5-750 mg/kg) or vehicle (ethanol/sucrose/physiological saline) were injected intravenously (i.v.) via tail vein or inferior vena cava at the end of the operation either as a single dose or sequentially (q24×3 doses). The natural mixture was compared with select sophorolipid derivatives (n=10-15 per group). Sham-operated animals served as non-sepsis controls. Survival rates were compared at 1 through 6 day post sepsis induction. The results showed sophorolipid treatment at 5 mg/kg body weight improved survival in rats with cecal ligation and puncture-induced septic shock by 28% at 24 h and 42% at 72 h for single dose, 39% at 24 h and 26% at 72 h for sequential doses, and 23% overall survival for select sophorolipid derivatives when compared with vehicle control (P<0.05 for sequential dosing) (FIG. 6). Toxicity was evident and dose-dependent with very high doses of sophorolipid (375-750 mg/kg body weight) with histopathology demonstrating interstitial and intra-alveolar edema with areas of micro-hemorrhage in pulmonary tissue when compared with vehicle controls (P<0.05). No mortality was observed in sham operated controls at all doses tested. Therefore, it was concluded that administration of sophorolipids after induction of intra-abdominal sepsis improves survival. The demonstration that sophorolipids can reduce sepsis-related mortality with different dosing regimens and derivatives provides continuing evidence toward a promising new therapy. New sophorolipid structures may be useful to improve their potency for treatment of sepsis.

Other work has shown that modified sophorolipids have antibacterial, antiviral, and anti-inflammatory properties (Mueller et al, 2006; Shah et al., 2005). In one example, sophorolipids were shown to down-regulate expression of proinflammatory cytokines including interleukin (Hagler et al. 2007). Furthermore, Table 1 below shows how antibacterial properties of sophorolipids can be increased by up to 1000 times relative to the natural SL mixture by simple modifications of sophorolipids such as esterification of fatty acid carboxyl groups and selective acetylation of disaccharide hydroxyl groups. Therefore, those skilled in the art will recognize that the changes in sophorolipid structure described herein can be used to improve sophorolipid-based therapeutics so they are more potent, less toxic, and have other desirable characteristics.

TABLE 1

|  | SL-E-9 $MIC_{100}$ | SL-A-4 $MIC_{100}$ | SL-E-4 $MIC_{100}$ | SL-E-5 $MIC_{100}$ | SL-E-1 $MIC_{100}$ | Natural SL $MIC_{100}$ |
|---|---|---|---|---|---|---|
| Eserichia coli | 1.67 | 5 | 5 | 5 | 1.67 | 5 |
| Moraxella | 1.67 | 5 | $2.05 \times 10^{-2}$ | $6.17 \times 10^{-2}$ | $6.17 \times 10^{-2}$ | 5 |
| Ralstoniaeutropha | 5 | 5 | 5 | 5 | 5 | 5 |
| Rhodoccocuserythropolis | N/A | 0.56 | $6.86 \times 10^{-3}$ | 5 | 5 | 5 |
| Salmonella choleraesuis | 5 | 5 | 5 | 5 | 1.67 | 5 |

Note:
All values in Table 1 are mg/ml. "Natural SL" refers to the mixture of acidic and lactonic sophorolipids obtained from fermenation. Strucures of sophorolipids are shown in FIG. 13.

Sophorolipids were shown to be useful for protection against human immunodeficiency virus (HIV) and as a vaginal topical microbicide (Shah et al, 2005). Thus far with the limited range of sophorolipid derivatives available, the sophorolipid diacetate ethyl ester derivative was found to be the most potent spermicidal and virucidal agent. Its virucidal activity against HIV and sperm-immobilizing activity against human semen are similar to those of nonoxynol-9. However, it also induces sufficient vaginal cell toxicity to raise concerns about its applicability for long-term microbicidal contraception. Therefore, those skilled in the art will recognize that the changes in sophorolipid structure described herein can be used to improve virucidal activity against HIV and sperm-immobilizing activity against human semen. Furthermore, new variants may reduce vaginal cell toxicity.

Sophorolipids were also found to mediate cytotoxic responses to pancreatic cancer cell lines (Fu et al., 2008). These anticancer responses were dose- and derivative-dependent and likely kill cancer cells by necrosis (FIG. 7 illustrates SL structure-activity relationships with HPAC cells). Furthermore, these agents are specific to cancer cells in that they did not affect normal human cells. Hence, sophorolipids represent a unique and novel class of drugs. New sophorolipid derivatives may be useful to increase their potency and specificity against pancreatic and other cancer types. Therefore, those skilled in the art will recognize that the changes in sophorolipid structure described herein can be used to improve the potency and specificity of sophorolipids against pancreatic and other cancer types.

Biopesticides

U.S. agriculture heavily relies on chemical pesticides for the eradication of plant pathogens. Each year farmers around the world spend approximately $30 billion on chemical pesticides whose use, while valuable for the control of plant pathogens, poses significant problems. Chemical pesticides harm non-target organisms including humans, domestic animals, beneficial insects and wildlife. Pesticide residues often remain on crops and accumulate in soil, water, and air. Chemical pesticides are almost exclusively petroleum-based which does not fit with current demands for products with increased bio-based content.

Biopesticides are generally segregated into microbial (fungal, bacterial and viral) and biochemical which include plant and insect growth regulators, pheromones, minerals, plant extracts and microbial extracts. Microbes have evolved natural chemical defense compounds which can be used for the control of microbial plant pathogens. One family of these compounds, microbial surfactants, are amphiphilic molecules produced using relatively simple and inexpensive procedures and substrates such as carbohydrates and lipids. They exist with a wide range of structures and are non-toxic or less toxic than chemical surfactants. Their natural occurrence in soil allows rapid acceptance from ecological and social viewpoints. Furthermore, the range of microbial surfactant structures and corresponding biological activities can be significantly extended through simple and efficient chemical modifications. The new sophorolipid compounds described herein will be useful in fine tuning sophorolipid biological properties and thereby developing sophorolipid derivatives that are highly effective against commercially important plant pathogens. Therefore, those skilled in the art will recognize that the changes in sophorolipid structure described herein can be used to improve sophorolipid biological activity against plant pathogens.

Previous Studies on Biopesticide Activity of Microbial and Chemical Biosurfactants Correll and co-workers investigated several ionic and non-ionic non-natural surfactants including fungicides azoxystrobin (Quadris) and 1,2,3-benzothiadiazole-7-carbothioic acid S-methyl ester (Actigard) in greenhouse and field tests. Indeed, several surfactants were shown to be highly effective in controlling white rust disease of spinach, caused by the oomycete pathogen *Albudooccidentalis* (FIG. 8). Several of these compounds are also effective on downy mildew of spinach, caused by the oomycete pathogen *Peronospora farinose*. These two pathogens are of greatest importance worldwide in protecting spinach crops.

Work by others highlights the potential of developing microbial biosurfactants as safe and effective biopesticides. For example, Stanghellini et al., while investigating control of root rot fungal infections on cucumbers and peppers caused by *Pythiumaphanidermatum* and *Phytophthoracapsici*, observed lysis of fungal zoospores. They postulated that cell lysis was due to a microbial surfactant in the nutrient solution. Subsequently, the bacterium was found to be *Pseudomonas aeruginosa*, a rhamnolipid (FIG. 9) biosurfactant producer. It was established that rhamnolipids have zoosporicidal activity against species of *Pythium, Phytophora*, and *Plasmopara* at concentrations ranging over 5 to 30 μg/mL. Rhamnolipids are believed to intercalate with and disrupt plasma membranes. Indeed, EPA Presidential Green Chemistry Awards were recently presented to Agraquest Inc. and Jeneil Biosurfactant Company for their work in developing rhamnolipid and lipopeptide biopesticide products, respectively.

Interestingly, both rhamnolipids, produced by *Pseudomonas aeruginosa*, and sophorolipids, produced by *Candida bombicola*, are glycolipids with closely related structures. As mentioned above, rhamnolipids were found to be effective biopesticides and these results led to their commercialization by Jeneil Biosurfactants Co., LLC. However, the highest volumetric yields of rhamnolipids thus far reported is 45 g/L, which is an order of magnitude lower than volumetric yields obtainable during sophorolipid fermentations (700 g/L). These facts, along with the convenient phase separation of sophorolipids in fermentors allowing their solvent-free isolation from fermentation broths, lead us to conclude that sophorolipids can be produced at lower costs than rhamnolipids. Yoo et al. reported that the sophorolipid natural mixture (non-chemically modified) is active against fungal plant pathogens *Phytophthoras* p. and *Pythium* sp. that are responsible for dumping-off disease. Inhibition of mycelial growth and zoospore motility was observed at 200 mg/L and 50 mg/L, respectively. Since the work by Yoo et al. is the only literature report of sophorolipid biopesticidal properties, the use of sophorolipids to mitigate plant pathogens remains largely unexplored. Furthermore, no work has been attempted to modify sophorolipids by simple and scalable chemical, enzymatic, or chemo-enzymatic methods in order to enhance their biopesticidal activity on important plant pathogens. Therefore, those skilled in the art will recognize that the changes in sophorolipid structure described herein can be used to improve the activity of sophorolipids against targeted plant pathogens.

In addition to their role in agriculture as antimicrobial agents, sophorolipids have a variety of applications in the cosmetics industry. First, as surfactants, they would be useful components in emulsifiers, cleansing and foaming agents. As antimicrobial agents, they would prolong the shelf-life of cosmetics as well as reduce the proliferation of bacteria. At present, Soliance markets formulations of sophorolipids derived produced in *Candida bombicola* from rapeseed oil. Soliance claims that natural origin sophorolipids target bacteria responsible for acne, dandruff, and body odors (Mager H, Röthlisberger R, Wagner F (1987). Furthermore, the use of sophorose-lipid lactone is claimed for the treatment of dandruffs and body odor (European patent 0209783). Therefore, those skilled in the art will recognize that the changes in sophorolipid structure described herein can be used to improve the activity of sophorolipids against targeted bacteria responsible for acne, dandruff and body odors and for the treatment of dandruff.

In addition to their antimicrobial properties, sophorolipids are claimed to have a variety of beneficial properties, including the stimulation of collagen synthesis, inhibition of free radical and elastase activity, stimulated wound healing and depigmentation. Hillion G, Marchal R, Stoltz C, Borzeix C F (1998), Use of a sophorolipid to provide free radical formation inhibiting activity or elastase inhibiting activity, U.S. Pat. No. 5,756,471 to Hillion et al.; PCT Patent Publication No. WO 99/62479 to Borzeix; U.S. Pat. No. 5,981,497 to Maingault. Therefore, those skilled in the art will recognize that further changes in sophorolipid structure described herein can be used to improve the ability of sophorolipids to stimulate collagen synthesis, inhibition of free radical and elastase activity, stimulate wound healing and depigmentation, and provide other desired characteristics for uses in cosmetics The synthesis of novel derivatives of sophorolipids of the kinds describe herein would widely expand the range of use of sophorolipids in cosmetic applications beyond those accessible to natural sophorolipids.

BRIEF SUMMARY OF THE INVENTION

Briefly stated, the present invention is new sophorolipid analog compositions of matter that can be used to inhibit bacterial and fungal growth, in therapeutics for the treatment of sepsis, cancer, viral infections such as HIV, as structure directing agents for self-assembled materials, as spermicidal substances, as an ingredient in cosmetic formulations that functions in various capacities such as emulsifiers, cleansing and foaming agents, targeting bacteria responsible for acne, dandruff, and body odors, stimulating collagen synthesis, inhibiting free radical formation, inhibiting elastase or stimulating skin fibroblast metabolism.

New sophorolipids and sophorolipid analogs disclosed herein include those having the formulas shown in FIG. 10 and having the structure:

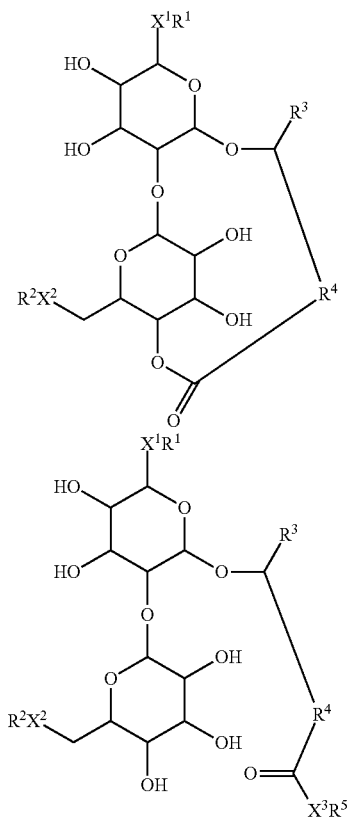

wherein $X^1 = X^2 = CH_2$

Selective (acetylation, acrylation) or non-selective (epoxide ring opening, electrophile addition)

In one embodiment:

$X^1$ or $X^2$ can be oxymethyl (—$CH_2O$—) or methylene (—$CH_2$—);

$R^1$ and/or $R^2$ can be selected from the following functional groups: hydrogen, acetyl, acryl, urethane, hydroxyalkyl, ether, halide, carboxyalkyl or alkyl containing heteroatoms (1°, 2°, and 3° amino, tetraalkylammonium, sulfate, phosphate);

Alternatively, $X^1$ or $X^2$ can be carbonyl (—C=O—) and $R^1$ and/or $R^2$ can be selected from the following groups: hydroxyl, amide, alkanamide, alkanamide containing heteroatoms (1°, 2°, and 3° amino, tetraalkylammonium), alkylsulfate, alkylphosphate, carbohydrate, mono- or oligopeptide;

$R^3$ can be a hydrogen or a methyl group;

$R^4$ is an alkyl chain that normally has 15 carbons but can have between 9 and 19 carbons and normally has one site that is unsaturated (C=C bond). Derivatives in this invention include modifying unsaturated (C=C) bonds within $R^4$ to be saturated (by hydrogenation), epoxidized, hydroxylated (by hydrolysis of the epoxide or hydroboration oxidation or dihydroxylation using osmium tetroxide), to a dithiirane, alkyl aziridine or cyclopropyl derivative. The methods involved in performing these chemical transformations are well known to those skilled in the art;

$X^3$ can contain heteroatoms (e.g., O, S, NH); and

The combination of $X^3R^5$ can be selected from the following functional groups: hydroxy, alkanethiolate, amide, alkanamide, alkanamide containing heteroatoms (1°, 2°, and 3° amino, tetraalkylammonium), alkylsulfate, alkylphosphate, carbohydrate, mono- or oligopeptide with 2-8 amino acids.

DETAILED DESCRIPTION OF PREFERRED EMBODIMENTS

Embodiments of this invention are based on the discovery that the administration of sophorolipids, sophorolipid analogs, and mixtures thereof can reduce the proliferation of bacteria and fungi; self-assemble and thereby direct or template the formation of new materials; be used as therapeutics for the treatment of sepsis, cancer and viral infections such as HIV; be applied and used as spermicidal agents; be used as an ingredient in cosmetic formulations that function in various capacities such as emulsifiers, cleansing and foaming agents, targeting bacteria responsible for acne, dandruff, and body odors, stimulating collagen synthesis, inhibiting free radical formation, inhibiting elastase or stimulating skin fibroblast metabolism. Embodiments of this invention include pure sophorolipids and/or new sophorolipid analogs as well as mixtures of sophorolipids and/or their derivatives. Embodiments of this invention also include carrying out two or more of the described modification methods on sophorolipid molecule so that changes in structure are carried out at multiple sites of sophorolipid molecules. It is understood that by variation in the structure of modified sophorolipids it is expected that the corresponding properties of sophorolipids can by modified, regulated, improved or fine-tuned. Thus, the modified sophorolipids disclosed herein will be useful in developing new products consisting of these modified sophorolipids and mixtures thereof. By proper selection from the modified sophorolipids described herein one can derive the desired self-assembly characteristics, biological properties in therapeutic applications, biological properties when in contact with skin for cosmetic formulations, and/or biological activity when in contact with various bacterial or fungal microorganisms. New sophorolipid derivatives are disclosed herein that further expand the range of modified sophorolipids that can be used in the above applications. It is understood that one skilled in the art will recognize that many variations can be made to the invention disclosed here without departing from the scope and spirit of the invention.

Figure 11:
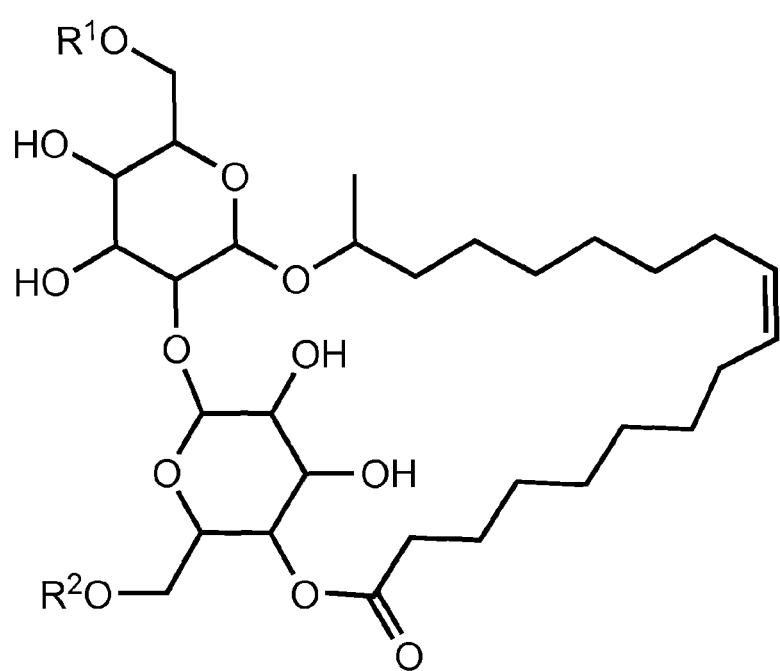
FIG. 11: Sophorolipids in the lactonic form.
Figure 12:
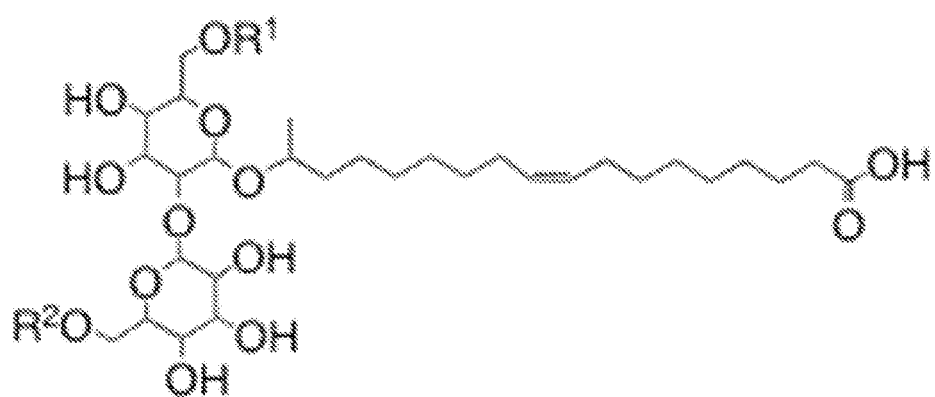
FIG. 12: Sophorolipids in the open chain (acidic) form.

The bio-based and modified sophorolipids that comprise the present invention are obtained from pure fatty acids, fatty acid mixtures, pure fatty acid ester, mixtures of fatty acid esters, and triglycerides along with triglyceride sources such as corn syrup, dextrins and glucose using a fermentation process comprising a wild-type or engineered yeast strain such as Candida bombicola. These sophorolipids generally consist of a hydrophilic carbohydrate head, sophorose, and a hydrophobic fatty acid tail with 16 or 18 carbon atoms. Sophorose is an unusual disaccharide that consists of two glucose molecules linked β-1,2. Furthermore, sophorose in sophorolipids can be acetylated on the 6'- and/or 6"-positions (FIG. 11). One fatty acid hydroxylated at the terminal or subterminal positions is β-glycosidically linked to the sophorose molecule (the polar head group). The fatty acid carboxylic acid group is either free (acidic or open form) or internally esterified generally at the 4"-position (lactonic form). The hydroxy fatty acid component of sophorolipids generally has 16 or 18 carbon atoms with generally one unsaturated bond (Asmer et al. 1988; Davila et al. 1993). However, the sophorolipid fatty acid can also be fully saturated. As such, sophorolipids synthesized by C. bombicola consist of a mixture of molecules that are related. Differences between these molecules are found based on the fatty acid structure (degree of unsaturation, chain length, and position of hydroxylation), existing in the lactonic or ring-opened form, and the acetylation pattern. Sophorolipids derivatives disclosed herein are described based on the predominant fatty acid constituent, 17-hydroxyoleic acid, produced by C. bombicola when fed crude oleic acid as its fatty acid source. However, sophorolipid derivatives disclosed herein can be prepared by using sophorolipids prepared from a wide range of fatty acid and carbohydrate feedstocks by a fermentation process.

Figure 13:
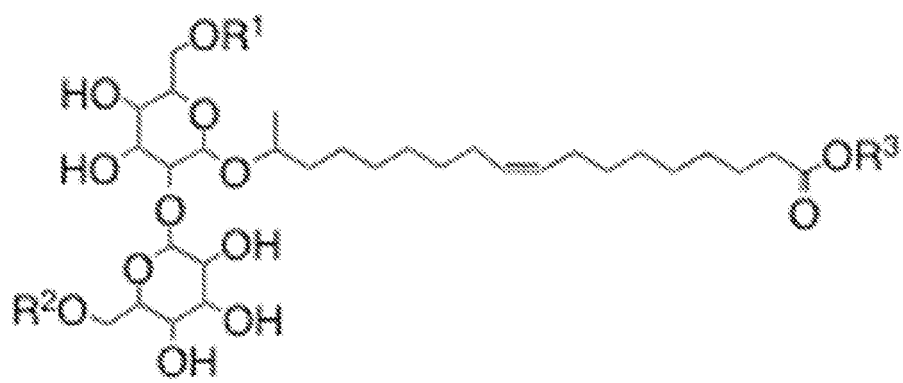
FIG. 13: Representative ester derivatives of the open chain form.
Figure 16:
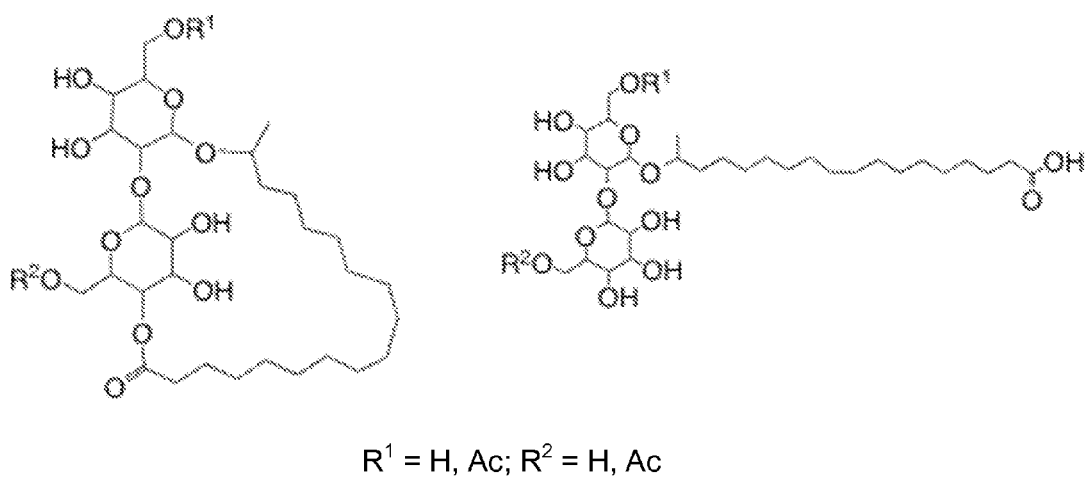
FIG. 16: Derivatives in which the C═C (double bond) in the lactonic and open chain forms have been hydrogenated.

One class of sophorolipid derivatives includes acidic sophorolipids esterified by the controlled alcoholysis of natural sophorolipid mixtures. Esters of varying chain lengths and with varying degrees of branching and containing a variety of heteroatoms are included in this invention (FIG. 13). A second class of sophorolipid derivatives includes lactonic and acidic sophorolipids in which the C=C bond has been reduced by hydrogen in the presence of a catalyst (FIG. 16). An exemplary reaction, applied to the conversion of lactonic sophorolipid (SL-L) to hydrogenated lactonic sophorolipid (SL-LH), is shown below.

Under a blanket of nitrogen in a 250 ml Parr bottle, a solution of lactonic sophorolipid mixture (5.00 g, 7.50 mmol in 75 ml 95% ethanol) was charged with 100 mg 10 wt % Pd/C added. The reactor was degassed and charged with 1 atm hydrogen. The reaction was allowed to run for 48 hours (the hydrogen pressure was periodically increased to 1 atm during this time). After 48 hours, the reaction mixture was filtered to remove the bulk of the Pd/C and the solution concentrated to dryness to afford white waxy crystals. $^1$H and $^{13}$C spectra indicate that the C=C bond has been reduced. (M/z=690.4, 648.4, 606.4).

Figure 14:
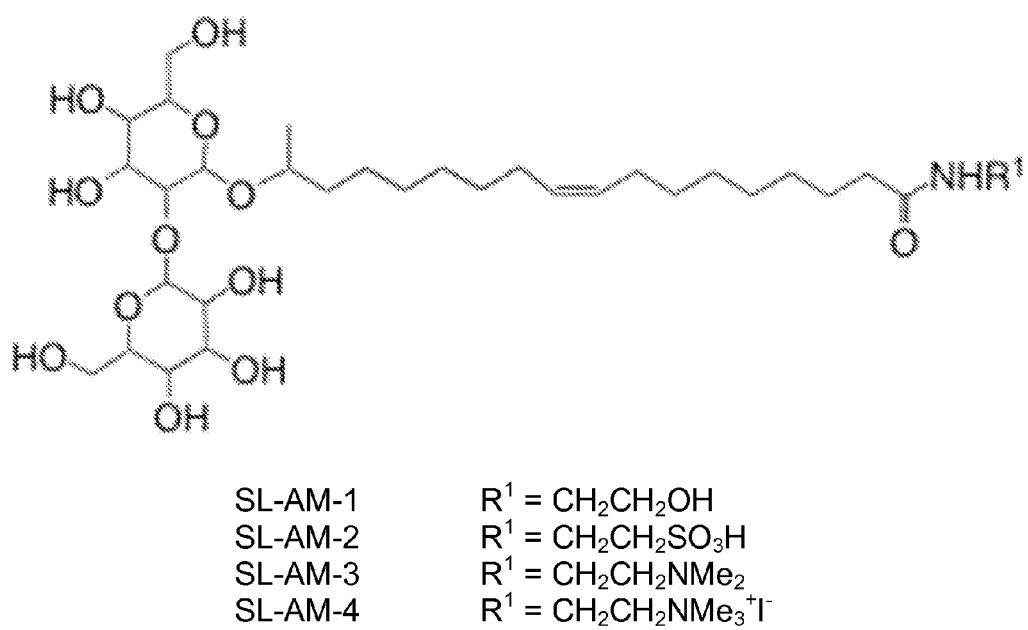
FIG. 14: Amide and related derivatives of the open chain form.
Figure 15:
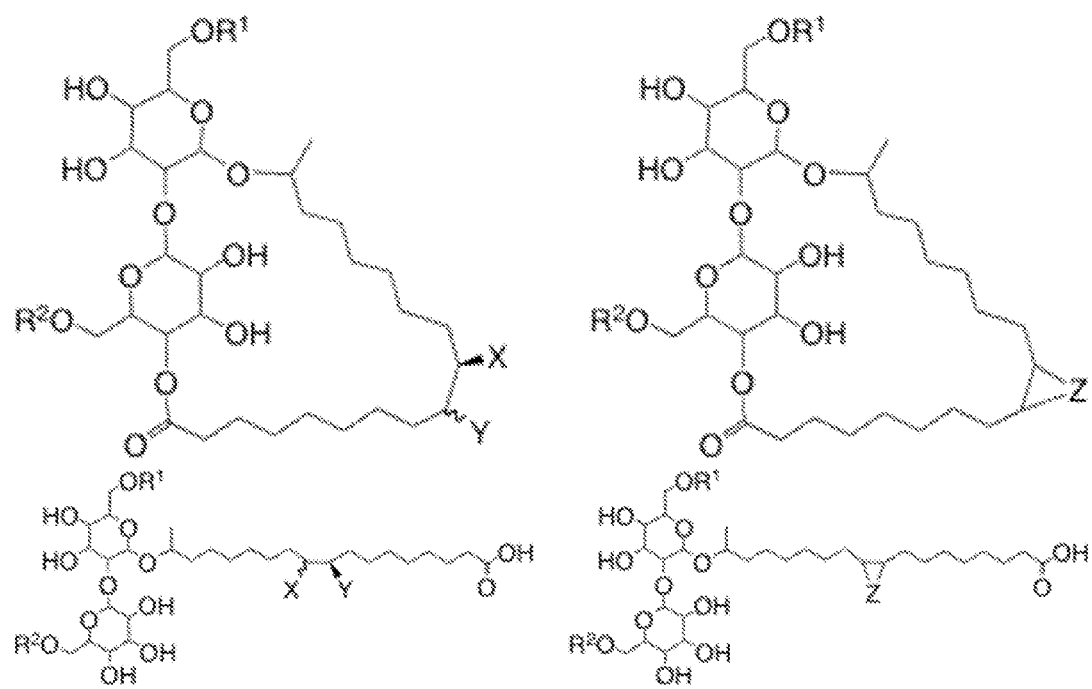
FIG. 15: Derivatives of the C═C (double bond) in the lactonic and open chain forms.
Figure 17:
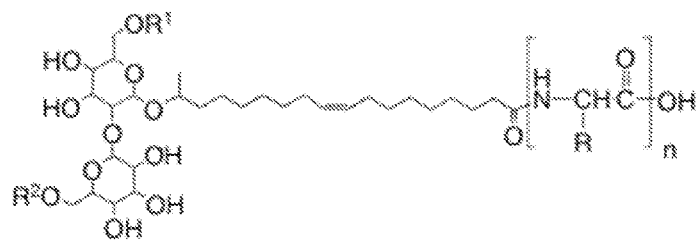
FIG. 17: Peptide derivatives of the open chain form.

A third class of sophorolipids includes amides of acidic sophorolipids, representative examples of which are shown in FIG. 14. In one exemplary reaction shown below, sophorolipid amides can be synthesized from an acidic sophorolipid methyl ester by treatment with an amine at elevated temperature. It is contemplated that a variety of amines, diamines, triamines of differing chain lengths containing aliphatic, olefinic, acetylenic, and aromatic substituents can be used to synthesize the corresponding amide derivatives. Additionally, inclusive of this invention are amines bearing ionic groups such as sulfate, sulfonate, phosphate, and quarternary ammonium salts that result in cationic or anionic charged head groups. Additionally, it is contemplated that a variety of substituted amino-containing compounds can be used as a platform for further functionalization and that amino acid and polypeptides of varying chain lengths can be incorporated (FIG. 17).

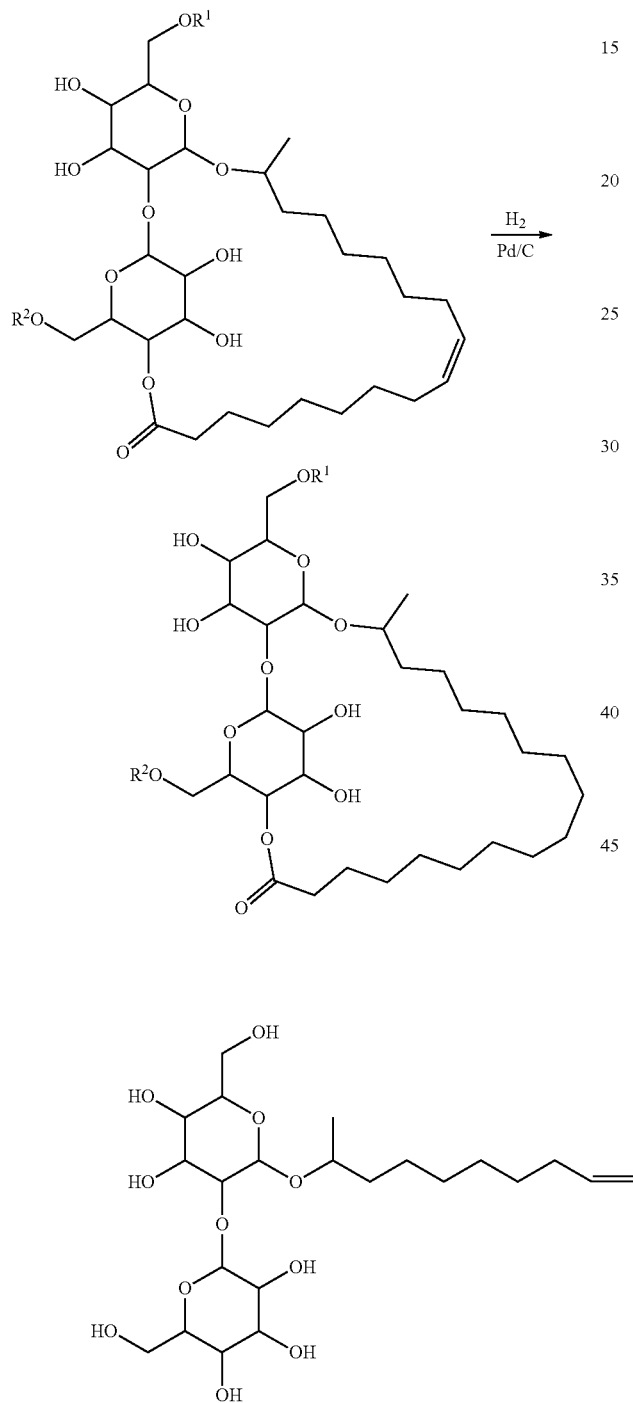

Synthesis of acidic sophorolipid N',N'-dimethylethylamide ((Z)-17-((4,5-dihydroxy-6-(hydroxymethyl)-3-((3,4,5-trihydroxy-6-(hydroxymethyl)tetrahydro-2H-pyran-2-yl)oxy)tetrahydro-2H-pyran-2-yl)oxy)-N-(2-(dimethylamino)ethyl)-octadec-9-enamide, SL-AM-3)

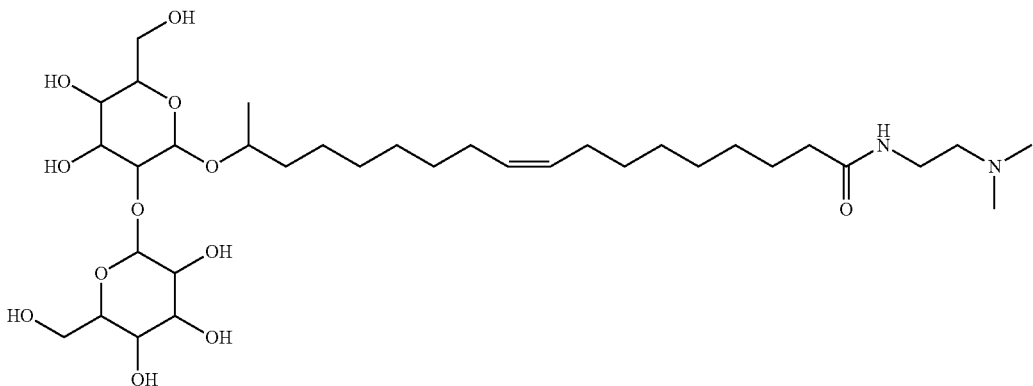

To 700 mg (1.1 mmol) sophorolipid methyl ester (SL-E1) was added N,N-dimethylethylenediamine (950 mg, 11 mmol, 10 equiv.). The reaction mixture was heated to 70° C. for 12 hours and concentrated to dryness (excess N,N-dimethylethylenediamine was removed in this step). The product was purified by flash chromatography (1:9 MeOH/CHCl$_3$) to afford 0.64 g (90% yield) yellow powder. M/z=692.59.

A fourth class of sophorolipids includes ammonium salts derived from N,N-dimethylethylamides. In one exemplary reaction shown below, a sophorolipid, N',N'-dimethylethylamide is converted into the corresponding ammonium salt by treatment of the amine with methyl iodide at elevated temperature.

Synthesis of acidic sophorolipid, N',N',N'-trimethylammoniumethylamide ((Z)-2-(17-((4,5-dihydroxy-6-(hydroxymethyl)-3-((3,4,5-trihydroxy-6 (hydroxyl methyl)tetrahydro-2H-pyran-2-yl)oxy)tetrahydro-2H-pyran-2-yl)oxy)octadec-9-enamido)-N,N,N-trimethylethanaminium iodide, SL-AM-4)

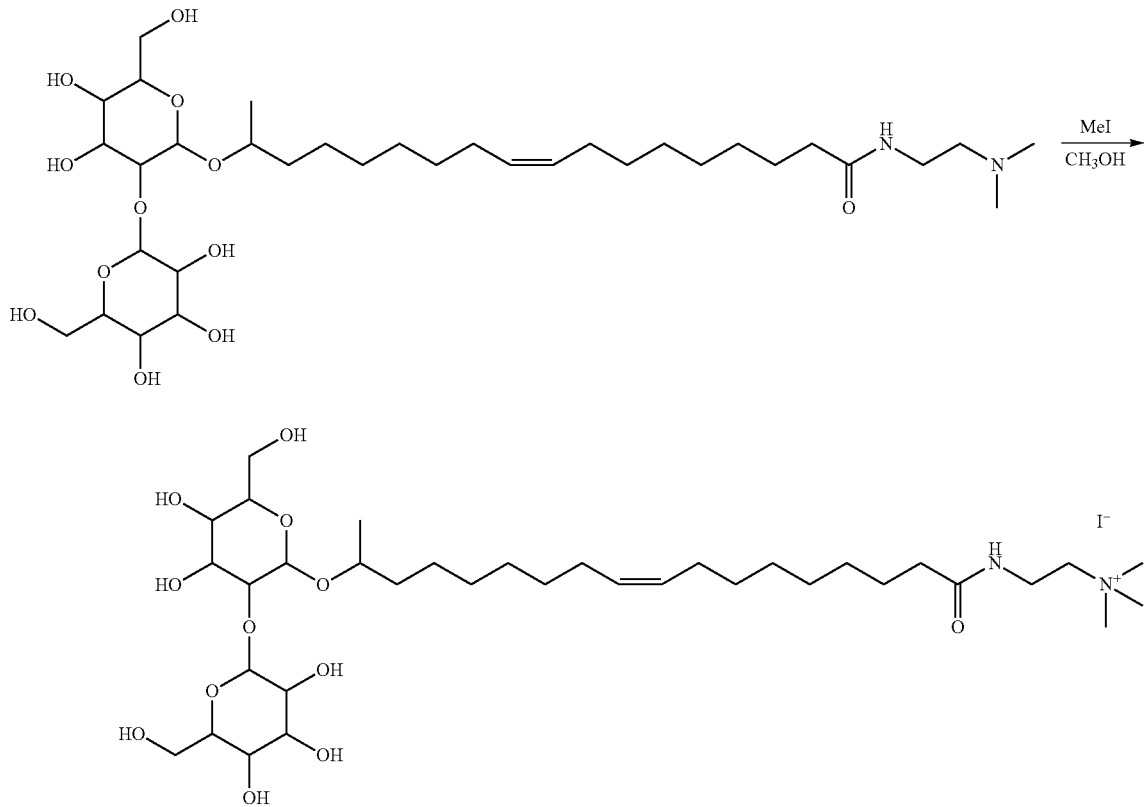

To 300 mg (0.43 mmol) sophorolipid N',N'-dimethylethylamide (SL-AM-3) was added methyl iodide (0.037 mL, 0.60 mmol, 1.4 equiv) in 2 mL methanol. The reaction mixture was heated to reflux temperature for 24 hours and concentrated in vacuo. The product was purified by flash chromatography (1:9 MeOH/CHCl3) to afford 0.255 g (85% yield) yellow powder. M/z=709 (M-I).

Figure 19:
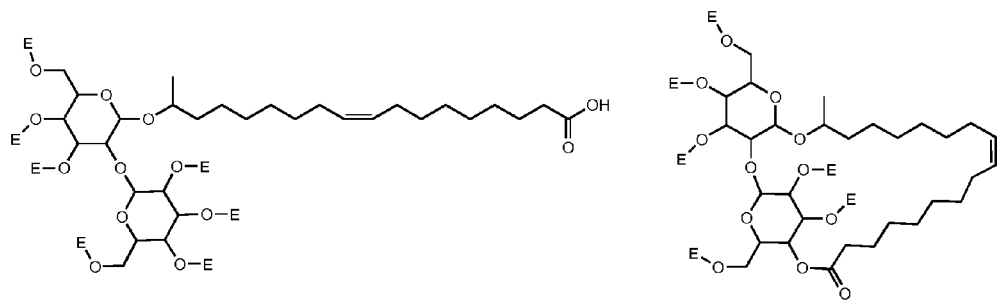
FIG. 19: Electrophile derivatives at sophorose ring.
Figure 20:
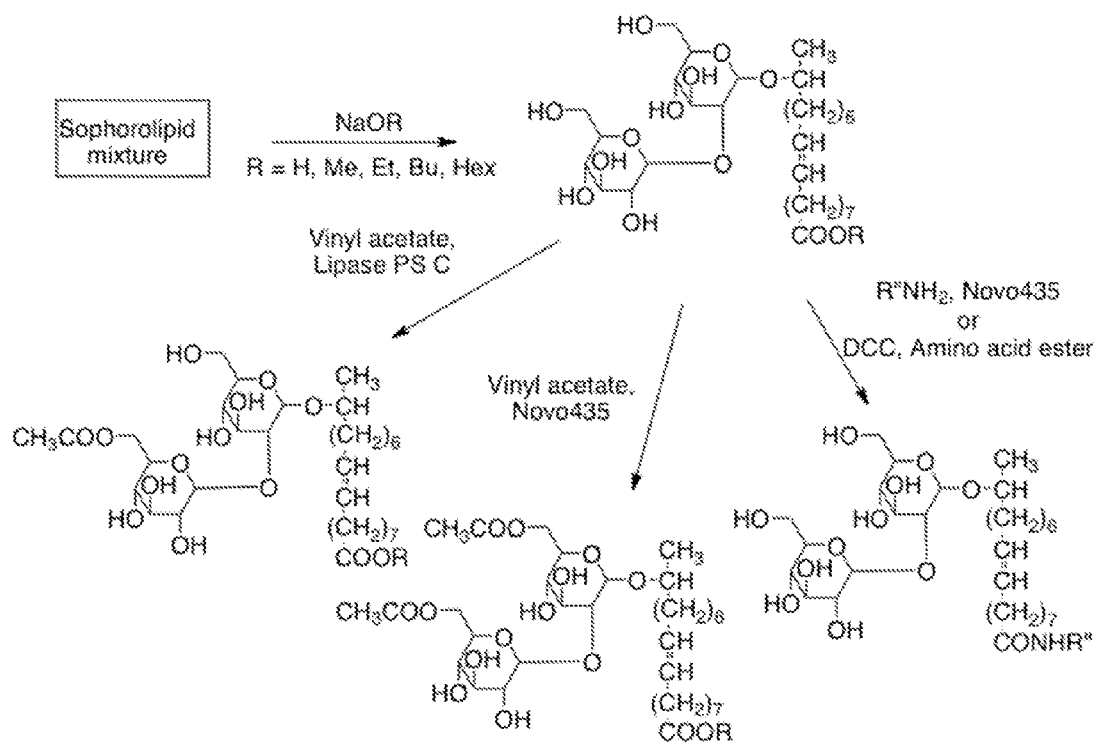
FIG. 20: Summary of chemo-enzymatic chemistry developed to prepare a library of sophorolipid analogs (see Azim et al., 2006; Singh et al., 2003; Bisht et al., 2000; Bisht et al. 1999).

A fifth class of sophorolipids include those modified at the sophorose 6' or 6" positions by, inter alia, an activated acyl molecule such as the vinyl ester or alkyl ester of propionic acid catalyzed by an enzyme catalyst such as a lipase in conjunction with one or more of the modifications described herein. In one exemplary reaction (Bisht et al., 1999), the unsubstituted acidic sophorolipid is acetylated at the sophorose 6' hydroxyl position. It is contemplated that carbonyl compounds of varying chain lengths and degrees of branching can be incorporated and that a variety of carbonyl-containing functional groups can be incorporated including succinate, malate and citrate. Additionally, it is contemplated that esters of amino acids and oligopeptides can be incorporated at the 6' and/or 6" positions of the sophorose ring. Finally, it is contemplated that the 6' and/or 6" positions of the sophorose ring may be alkylated (FIG. 19) by ethylene oxide or a substituted alkylene oxide such as 2,3-epoxypropyl-1,1,1-trimethylammonium chloride (Quab151) or related electrophiles as described in D. B. Solarek: Cationic Starches, in *Modified Starches: Properties and Uses* (Ed. O. B. Wurzburg), 1989. Such substitutions will likely occur at the 1° 6' and/or 6" positions but may also occur at the 2° sophorose ring hydroxyls to generate mixtures of sophorolipid derivatives.

Dihydroxylation of Lactonic Sophorolipid

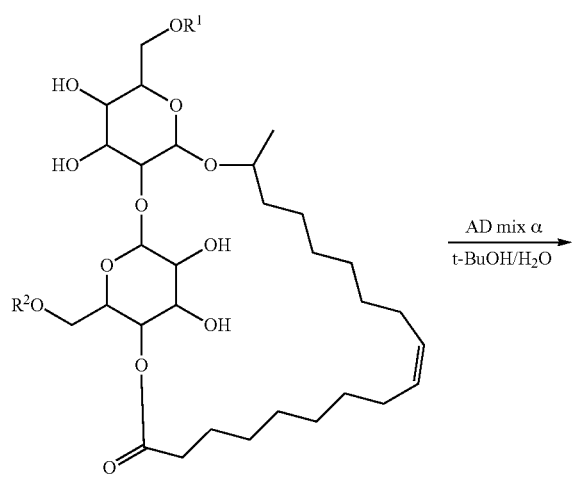
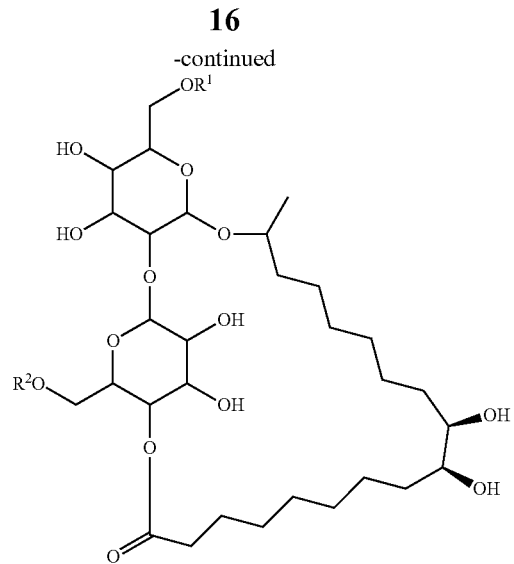

Figure 1:
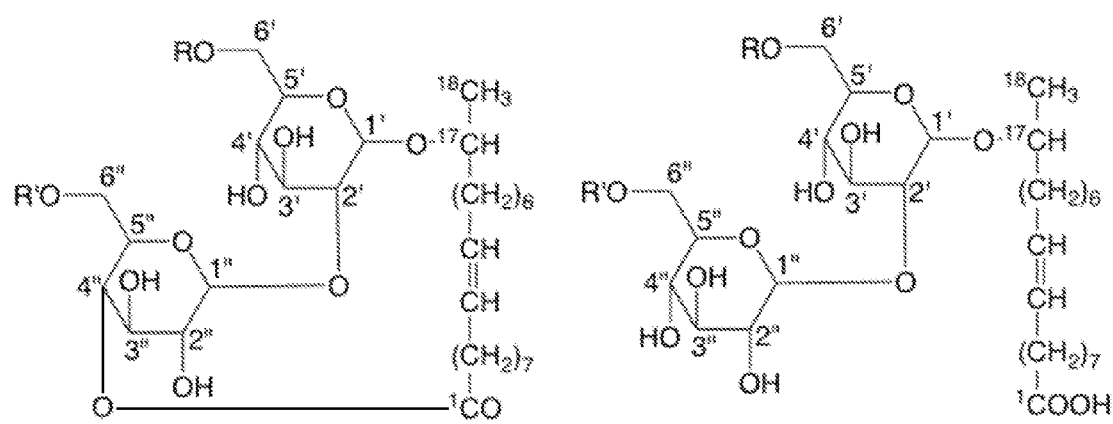
FIG. 1: Structure of lactonic and acidic forms of sophorolipid mixture produced by Candida bombicola.
Figure 2:
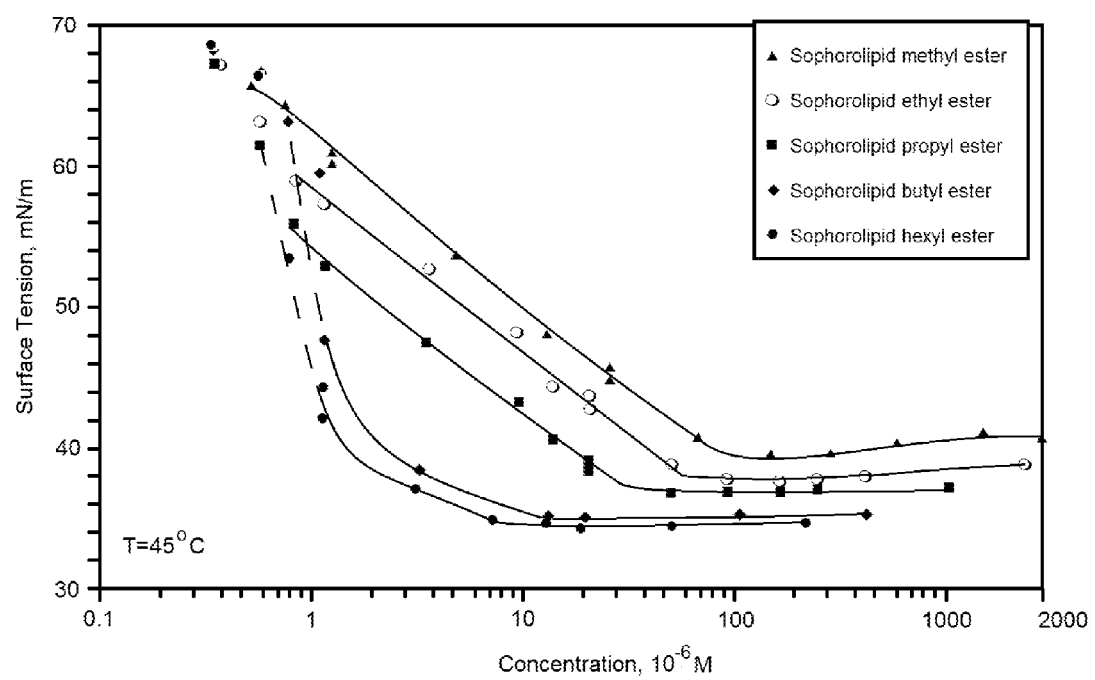
FIG. 2: Surface tension of sophorolipid esters.
Figure 3:
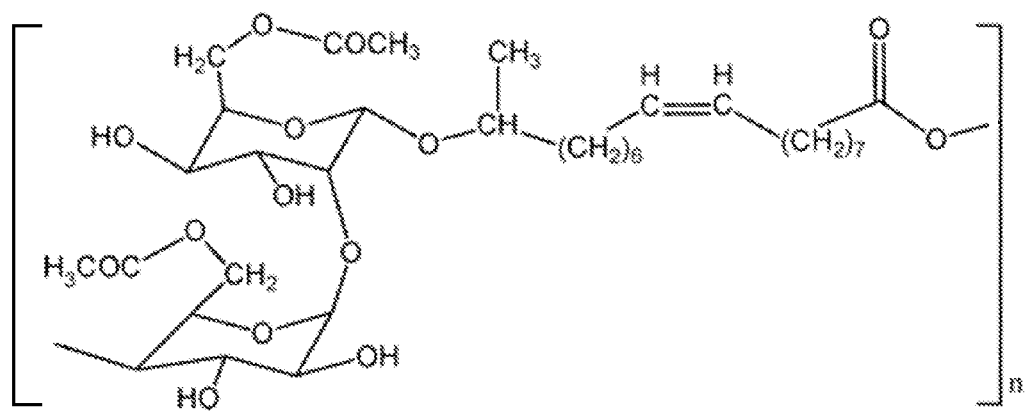
FIG. 3: Metathesis ring-opening polymerization of natural lactonic sophorolipids (SL) gives poly(SL) with alternating C18 oleic acid and bulky diacetylated sophorose units.
Figure 4:
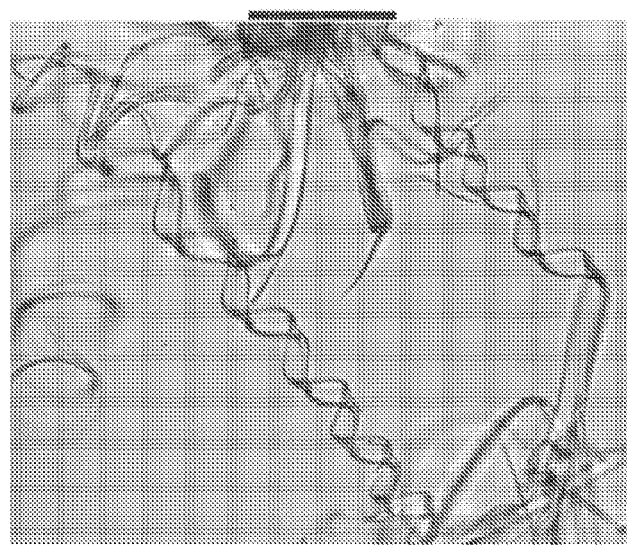
FIG. 4: Free acidic SL dissolved in dilute HCl, final pH=4.1, C=2.2 mg/mL. Big helical ribbons (e.g., ~11 μm wide and hundreds μm long) were observed.
Figure 5:
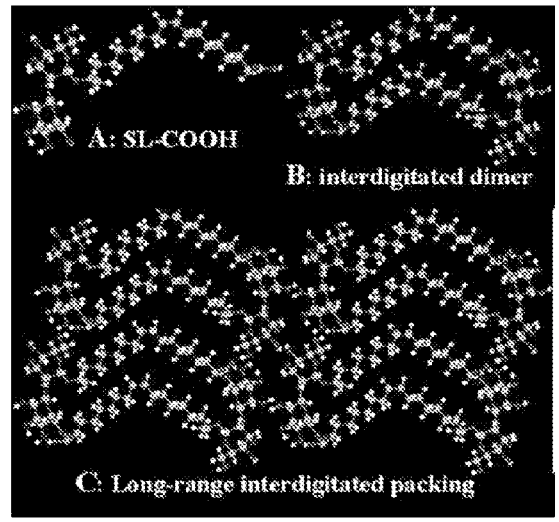
FIG. 5: Molecular modeling of SL-COOH molecules (A) and a possible interdigitated lamellar packing model of SL-COOH molecules in the giant ribbons (C).
Figure 6:
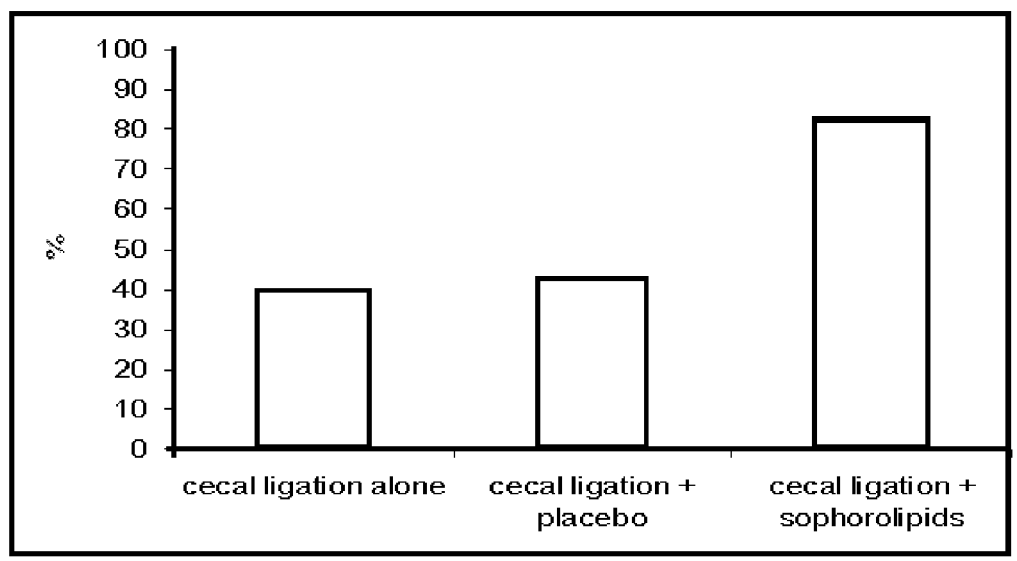
FIG. 6: SLs improved the survival rate of Sprague Dawley rats who were in septic shock due to cecal ligation and puncture.
Figure 7:
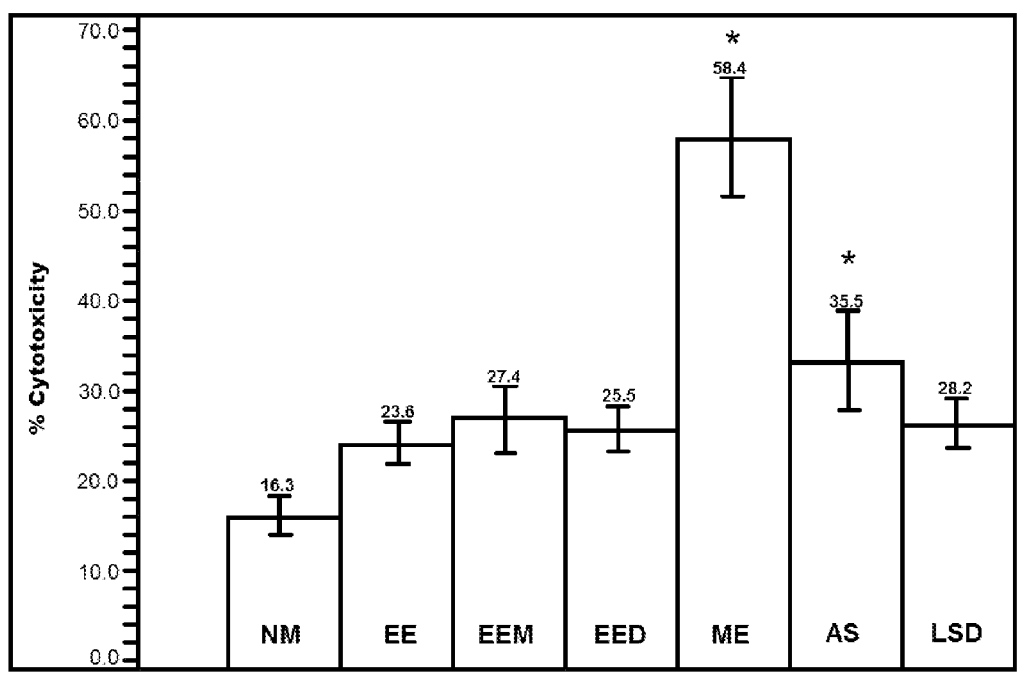
FIG. 7: Cytotoxicity of sophorolipid and derivatives: HPAC cells were cultured with 100 μg of sophorolipid natural mixture or select derivatives. Cytotoxicity was determined as described in Materials and methods. Data are presented as mean of three experiments and are reported as percent cytotoxicity ±SE and significance determined by Student's t-test; *$P \leq 0.05$ compared with natural mixture (SL mix). SL mix=natural mixture; SL EE=ethyl ester; SL EEM=ethyl ester monoacetate; SL EED=ethyl ester diacetate; SL ME=methyl ester; AS=acidic sophorolipid; LSD=lactonic sophorolipid diacetate.
Figure 8:
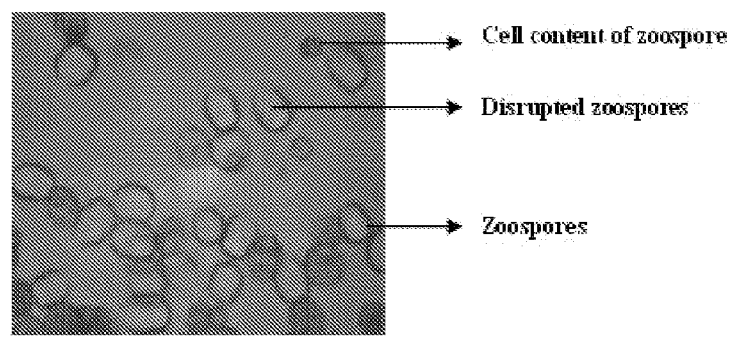
FIG. 8: Lysis of Albudooccidentalis zoospores by synthetic biosurfactants in combination with fungicide. Photograph provided courtesy of Prof. Correll (University of Arkansas).
Figure 9:
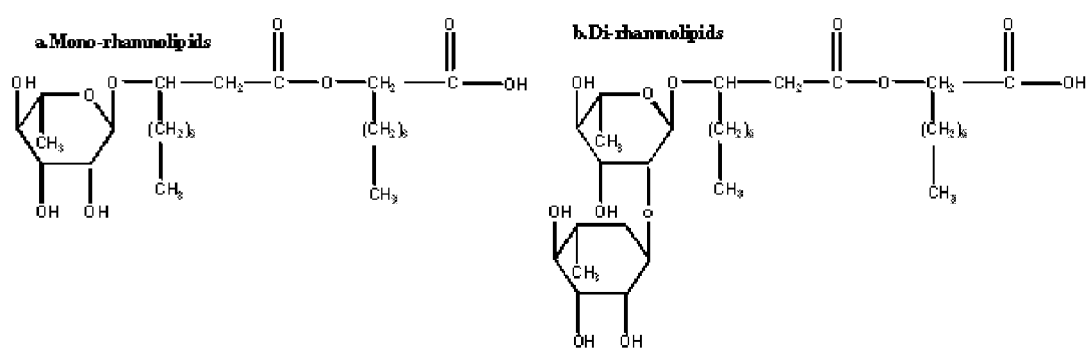
FIG. 9: Structures of natural mixture rhamnolipids produced by Pseudomonas aeruginosa.
Figure 10:
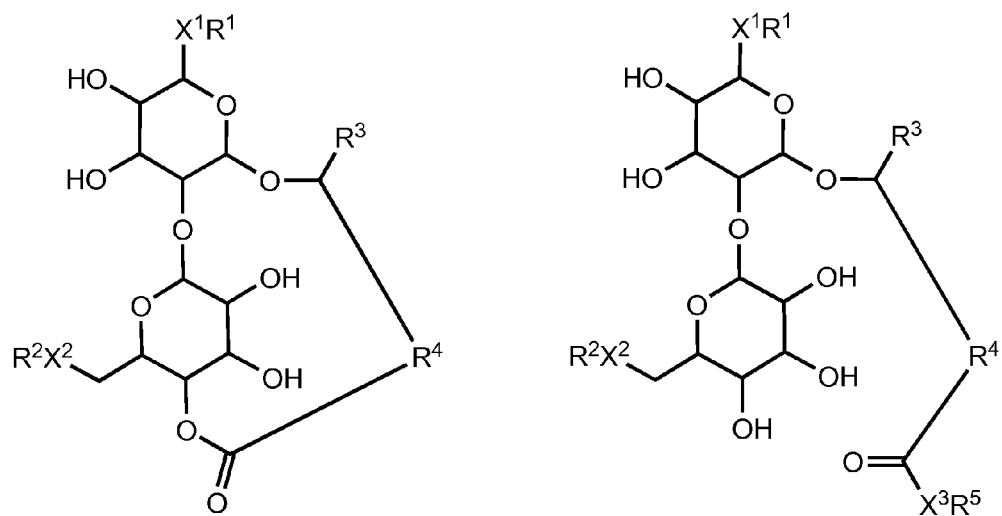
FIG. 10: Formulas for new sophorolipids and sophorolipid analogs of the present invention.
Figure 18:
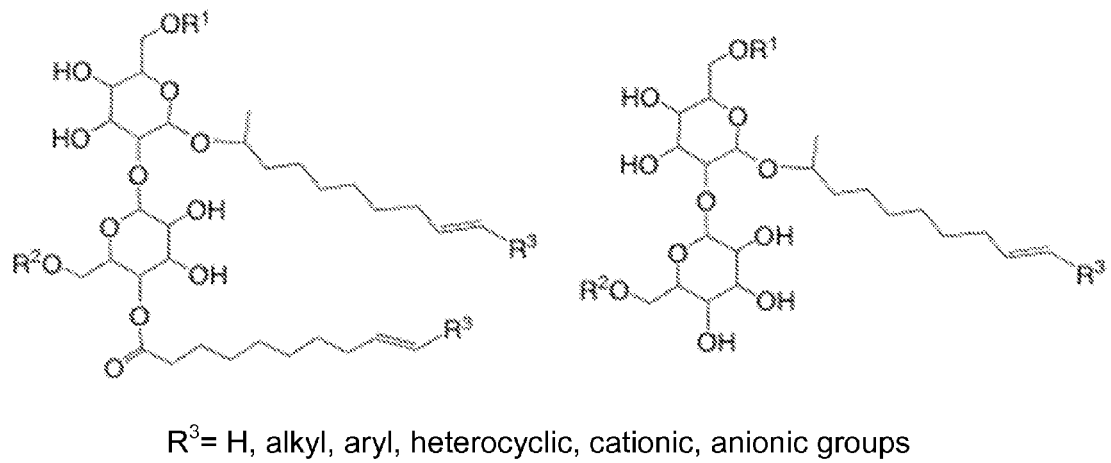
FIG. 18: Trans alkylidenation derivatives of the lactonic form and open chain.

To a suspension of lactonic sophorolipid mixture (4 compounds: 6',6"-dihydroxy, 6'-acetyl, 6"-acetyl, 6',6"-diacetyl (which can be generally acyl groups with variable carbon chain lengths), 200 mg total, ca. 0.310 mmol, based on monoacetylated derivative mass) in 10 mL 1:1 tert-butanol/H2O at 0° C. was added methane sulfonamide (29.5 mg, 0.310 mmol), followed by 434 mg AD mix α, (a formulation consisting of potassium osmate dihydrate, potassium ferrocyanide, potassium carbonate, and a chiral auxiliary ligand). The reaction mixture was maintained at 0° C. overnight. After 15 hours, the reaction mixture was allowed to warm to room temperature and sodium thiosulfate (450 mg) was added. The reaction mixture was extracted in 3×15 mL diethyl ether, dried over MgSO4, and evaporated to produce 145 mg (70%, based on the monoacetyl derivative) of a colorless oil. $^1$H and $^{13}$NMR reveal that the C=C has been fully reduced. M/z=XX A sixth class of sophorolipids include those formed from transalkylidenation of the C=C within $R^4$ (FIG. 10) of lactonic or acidic sophorolipids. Novel compounds in this class include alkenes with linear or branched alkyl substituents. Compounds in which the double bond is substituted by aryl, heterocyclic, cationic or anionic or neutral groups containing heteroatoms is contemplated (FIG. 18). $R^3$=H, alkyl, heterocycle (see below).

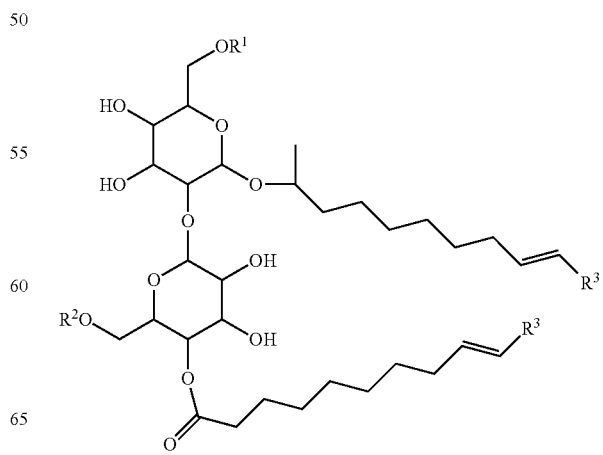

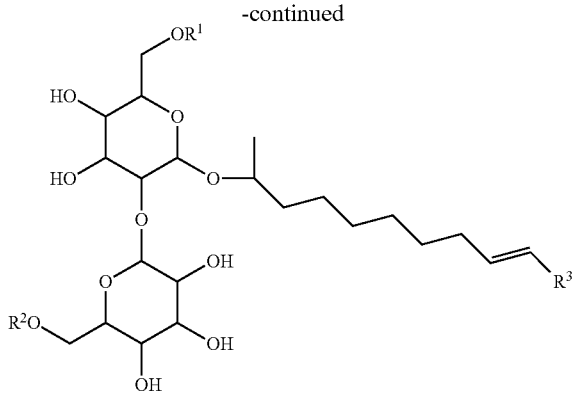

Example 1

The hydrogenated lactonic sophorolipids have antifungal activity, which were confirmed by experiment and observations. Sophorolipid samples were dissolved in 5% ethanol solution to a final concentration of 5 mg/mL and used as a stock solution. The stock solution (100 μl) was added into a 96 well microplate and serially diluted from 2.5 mg/ml to 0.0024 mg/ml using culture medium. After serial dilution, 80 μl of fresh culture medium and 20 μl of spore suspension were added to each well and the plates were incubated for 7 days. The minimum inhibitory concentration (MIC) was determined to measure antifungal activity of sophorolipid-derived compounds. MIC values for antifungal activity were determined by absence of visible growth in the micro wells containing sophorolipid after 7 days of incubation. Natural and lactonic SLs were active against four pathogens, whereas hydrogenated lactonic and acidic SLs active against three and two pathogens respectively. In several cases, hydrogenated sophorolipids showed comparable or better inhibition to fungal growth versus natural sophorolipids. The results are shown in Table 2.

TABLE 2

Antifungal activity of natural (SN-L), lactonic (SL-L) and hydrogenated lactonic (SL-LH) and hydrogenated natural (SL-H) Sophorolipids

| Pathogen | SL-N | SL-L | SL-LH | SL-H |
|---|---|---|---|---|
| | | MIC mg/mL | | |
| Alternariatomatophilia | 2.5 | — | 2.5 | — |
| A. solani | 2.5 | — | — | — |
| A. alternate | 2.5 | 2.5 | 2.5 | — |
| Fusarimoxysporium | — | 2.5 | — | — |
| Botrytis cinerea | — | 2.5 | 0.6 | — |
| Phytophthorainfestans | — | — | — | 2.5 |
| Ustilagomaydis | — | — | — | — |
| Phytophthoracapsici | 1.25 | 0.6 | — | 0.6 |

Example 2

The acidic sophorolipid esters have antifungal activity, which were confirmed by experiment and observations. Sophorolipid samples were dissolved in 5% ethanol solution to a final concentration of 5 mg/mL and used as a stock solution. The stock solution (100 μl) was added into a 96 well microplate and serially diluted from 2.5 mg/ml to 0.0024 mg/ml using culture medium. After serial dilution, 80 μl of fresh culture medium and 20 μl of spore suspension were added to each well and the plates were incubated for 7 days. The minimum inhibitory concentration (MIC) was determined to measure antifungal activity of sophorolipid-derived compounds. MIC values for antifungal activity were determined by absence of visible growth in the micro wells containing sophorolipid after 7 days of incubation. These results show that methyl (SL-E-1) and butyl esters (SL-E-3) actively inhibited the growth of three pathogens while other esters (SL-E-4,5,6, and 8) are active against one of the pathogens. In several cases, acidic sophorolipid esters showed comparable or better inhibition of fungal growth versus natural sophorolipids. The results are shown in Table 3.

TABLE 3

Antifungal activity of sophorolipid ester derivatives[a]

| Pathogen | SL-E-1 | SL-E-2 | SL-E-3 | SL-E-4 | SL-E-5 | SL-E-6 | SL-E-8 |
|---|---|---|---|---|---|---|---|
| | | | MIC mg/mL | | | | |
| Alternariatomatophilia | — | — | 0.15 | — | — | — | — |
| A. solani | 2.5 | — | 1.25 | — | — | — | 1.25 |
| A. alternate | — | — | — | — | — | — | — |
| Fusarimoxysporium | 2.5 | — | — | — | — | — | — |
| Botrytis cinerea | — | — | — | — | — | — | — |
| Phytophthorainfestans | — | — | 1.25 | — | — | — | — |
| Ustilagomaydis | — | — | — | — | — | — | — |
| Phytophthoracapsici | 1.25 | — | — | 0.6 | 0.6 | 0.6 | — |

[a]Structures of sophorolipid ester derivatives are shown in FIG. 13.

Example 3

The acidic sophorolipid amide derivatives have antifungal activity, which were confirmed by experiment and observations. Sophorolipid samples were dissolved in 5% ethanol solution to a final concentration of 5 mg/mL and used as a stock solution. The stock solution (100 μl) was added into a 96 well microplate and serially diluted from 2.5 mg/ml to 0.0024 mg/ml using culture medium. After serial dilution, 80 μl of fresh culture medium and 20 μl of spore suspension were added to each well and the plates were incubated for 7 days. The minimum inhibitory concentration (MIC) was determined to measure antifungal activity of sophorolipid-derived compounds. MIC values for antifungal activity were determined by absence of visible growth in the micro wells containing sophorolipid after 7 days of incubation. Among all sophorolipids screened for antifungal activity, the family of amide derivatives shows high activity against four pathogens. Two of the amides, SL-AM-3 and 4 showed growth inhibitory activity against four pathogens, *Alternariatomatophilia, A. solani, A. alternate* and *Botrytis cinerea*. The results are shown in Table 4.

TABLE 4

Antifungal activity of sophorolipid amide derivatives[a]

| Pathogen | SL-AM-1 | SL-AM-3 MIC mg/mL | SL-AM-4 |
|---|---|---|---|
| *Alternariatomatophilia* | 2.5 | 0.3 | 0.15 |
| *A. solani* | — | 0.15 | 0.6 |
| *A. alternate* | — | 1.25 | 1.25 |
| *Fusarimoxysporium* | — | — | — |
| *Botrytis cinerea* | 2.5 | 0.6 | 0.6 |
| *Phytophthorainfestans* | — | — | — |
| *Ustilagomaydis* | — | — | — |
| *Phytophthoracapsici* | — | — | — |

[a]Structures of sophorolipid amide derivatives are shown in FIG. 14.

This demonstrates that by using new modified sophorolipid compositions of matter that are hereby incorporated within this invention, sophorolipid properties such as an improvement in a biological activity can be achieved. In the above example the modified sophorolipid analog new compositions of matter described herein were used to identify compounds with enhanced activity against important plant pathogenic microorganisms. It is understood that modified sophorolipid analogs can be used in pure form, admixed with one or more derivatives, admixed with one or more natural sophorolipids. Furthermore, the modifications described herein can be performed at different parts of sophorolipid molecules to enhance the number of members of new sophorolipid derivatives that are part of this invention.

The above detailed description of the embodiments, and the examples, are for illustrative purposes only and are not intended to limit the scope and spirit of the invention, and its equivalents, as defined by the appended claims. One skilled in the art will recognize that many variations can be made to the invention disclosed in this specification without departing from the scope and spirit of the invention. As a single example, one skilled in the art of organic synthesis can use combinations of synthetic techniques described herein to synthesize an acidic sophorolipid amide derivative in which the C=C double bond has been hydrogenated.

REFERENCES

Bluth M H, Fu S L, Fu A, Stanek A, Smith-Norowitz T A, Wallner S R, Gross R A, Nowakowski M, Zenilman M E "Sophorolipids decrease asthma severity and ova-specific IgE production in a mouse asthma model" *Journal of Allergy and Clinical Immunology*, 121 (2), Pages: S2-S2, Supplement: Suppl. 1, Meeting Abstract: 6 (FEB 2008)

Fu S L, Wallner S R, Bowne W B, Hagler, M D; Zenilman, M E; Gross, R. A., Bluth, M H. Sophorolipids and their derivatives are lethal against human pancreatic cancer cells, *Journal of Surgical Research* 148 (1), 77-82 (2008).

Zini E, Gazzano M, Scandola M, Wallner, S. R. Gross, R. A. Glycolipid Biomaterials: Solid-State Properties of a Poly (sophorolipid). *Macromolecules* 42(20) 7463-7468 (2008).

Hardin, R.; Pierre, J.; Schulze, R.; Mueller, C. M.; Fu, S. L.; Wallner, S. R.; Stanek, A.; Shah, V.; Gross, R. A.; Weedon, J.; Nowakowski, M.; Zenilman, M. E.; Bluth, M. H., Sophorolipids improve sepsis survival: Effects of dosing and derivatives. *Journal of Surgical Research*, 142 (2), 314-319 (2007). (PDF)

Fu, S. L.; Mueller, C.; Lin, Y. Y.; Viterbo, D.; Pierre, J.; Shah, V.; Gross, R.; Schulze, R.; Zenilman, M., Sophorolipid treatment decreases LIPS induced inflammatory responses and NO production in macrophages. *Journal of the American College of Surgeons*, 205 (3), S44-S44 (2007). (PDF)

Hagler, M.; Smith-Norowitz, T. A.; Chice, S.; Wallner, S. R.; Viterbo, D.; Mueller, C. M.; Gross, R.; Nowakowski, M.; Schulze, R.; Zenilman, M. E.; Bluth, M. H., Sophorolipids decrease IgE production in U266 cells by downregulation of BSAP (Pax5), TLR-2, STAT3 and IL-6. *Journal of Allergy and Clinical Immunology*, 119 (1), S263-S263 (2007). (PDF)

Felse, P. A.; Shah, V.; Chan, J.; Rao, K. J.; Gross, R. A., Sophorolipid biosynthesis by *Candida bombicola* from industrial fatty acid residues. *Enzyme and Microbial Technology*, 40 (2), 316-323 (2007). (PDF)

Wei Gao, Rena Hagver, Vishal Shah, Wenchun Xie, Richard A. Gross, M. Firatllker, Chrissy Bell, Kelly A. Burke, and E. Bryan Coughlin Glycolipid Polymer Synthesized from Natural Lactonic Sophorolipids by Ring-Opening Metathesis Polymerization *Macromolecules*, 40(2), 145 (2006). (PDF)

Bluth, M. H.; Kandil, E; Mueller, C. M.; Shah, V.; Lin, Y. Y.; Zhang, H; Dresner, L.; Lempert, L.; Nowakowski, M.; Gross, R; Schulze, R.; Zenilman, M. E. Sophorolipids block lethal effects of septic shock in rats in a cecal ligation and puncture model of experimental sepsis, *Critical Care Medicine* 34 (1): 188-195 (2006). (PDF)

Mueller, C. M.; Viterbo, D.; Murray, P. J.; Shah, V.; Gross, R.; Schulze, R.; Zenilman, M. E.; Bluth, M. H. Sophorolipid treatment decreases inflammatory cytokine expression in an in vitro model of experimental sepsis. *Faseb Journal* 20 (4): A204-A204 Part 1, (2006). (PDF)

Azim, A; Shah, V.; Doncel, G. F.; Peterson, N.; Gao, W.; Gross, R. Amino acid conjugated sophorolipids: A new family of biologically active functionalized glycolipids. *Bioconjugate Chemistry* 17 (6): 1523-1529 (2006). (PDF)

Shah V, Doncel G F, Seyoum T, Eaton K M, Zalenskaya I, Hagver R, Azim A, Gross R. Sophorolipids, microbial glycolipids with anti-human immunodeficiency virus and sperm-immobilizing activities. *Antimicrob Agents Chemother*, 149; 1-8 (2005). (PDF)

Zhang, L., Somasundaran, P., Singh, S. K., Felse, A. P., Gross, R. A. Synthesis and interfacial properties of sophorolipid derivatives *Colloids and Surfaces A: Physicochem. Eng. Aspects;* 240; 75-82 (2004). (PDF)

Zhou, S., Xu, Chang., Wang, J., Gao, W., Akhverdiyeva, R., Shah, V., Gross, R. A. Supramolecular Assembles of a Naturally Derived Sophorolipid. *Langmuir*, 20; 7926-7932 (2004). (PDF)

Singh, S, K, Felse, A. P., Nunez, A., Foglia, T. A. and Gross, R. A. Regioselective Enzyme-Catalyzed Synthesis of Sophorolipid Esters, Amides and Multifunctional Monomers. *J. Org. Chem.;* 68; 5466-5477 (2003). (PDF)

V Guilmanov, A Ballistreri, G Impallomeni, R. A. Gross, "Oxygen Transfer Rate and Sophorose Lipid Production by *Candida bombicola*", *Biotechnol. and Bioeng;* 77(5), 489-494 (2002). (PDF)

K. S. Bisht, W Gao, R. A. Gross, "Glycolipids from *Candida bombicola*: Polymerization of 6-O-Acryl Sophorolipid Derivative", *Macromolecules*, 33, 6208-6210 (2000). (PDF)

K. Bisht, R. Gross and D. Kaplan, "Enzyme-Mediated Regioselective Acylations of Sophorolipids", *J. Org. Chem.*, 64:3, 780-789 (1999). (PDF)

ADDITIONAL REFERENCES

Gross, R. A., Treatment and prophylaxis of sepsis and septic shock with sophorolipids. 2004, (Polytechnic University, USA). Application: US p. 10 pp.

Wadgaonkar, R., et al., Lung injury treatment with sophorolipids. 2008, (The Research Foundation of State University of New York, USA). Application: WO p. 29 pp.

Gross, R. A. and V. Shah, Antimicrobial properties of various forms of sophorolipids. 2004, (Polytechnic University, USA). Application: WO p. 40 pp.

Gross, R. A. and V. Shah, Anti-herpes virus properties of various forms of sophorolipids. 2007, (Polytechnic University, USA). Application: WO p. 18 pp.

Gross, R. A., V. Shah, and G. F. Doncel, Spermicidal and virucidal properties of various forms of sophorolipids produced by *Candida bombicola*. 2004, (USA). Application: US p. 9 pp.

Gross, R. A. and M. N. Bluth, Sophorolipids for the treatment and prophylaxis of cancer. 2009, (USA). Application: US p. 9 pp.

What is claimed is:

1. Sophorolipids and sophorolipid analogs having the following formulas:

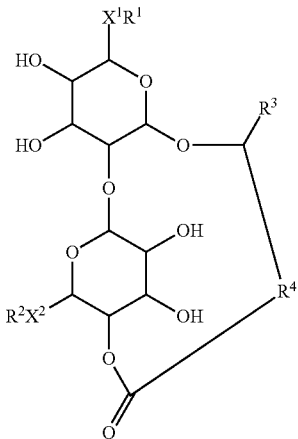

-continued

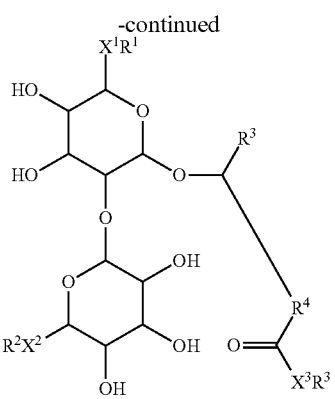

wherein:

$X^1$ or $X^2$ are carbonyl (—C=O—);

$R^1$ and/or $R^2$ are selected from the groups consisting of: hydroxyl; amide; alkanamide; alkanamide containing heteroatoms 1°, 2°, and 3° amino, or tetraalkylammonium; alkylsulfate; alkylphosphate; carbohydrate; and mono- or oligopeptide with 2-8 amino acids;

$R^3$ is a hydrogen or a methyl group;

$R^4$ is an alkyl chain that has between 9 and 19 carbons and has one site that is an unsaturated C=C bond which can occur as a hydrogenated, hydroxylated, epoxy, dithiirane, alkyl aziridine or cyclopropyl derivative;

$X^3$ contains heteroatoms selected from the group consisting of O, S, and NH; and the combination of $X^3R^5$ is selected from the functional groups consisting of: hydroxy; alkanethiolate; amide; alkanamide; alkanamide containing heteroatoms 1°, 2°, and 3° amino, or tetraalkylammonium; alkylsulfate; alkylphosphate; carbohydrate; and mono- or oligopeptide.

2. The sophorolipids and sophorolipid analogs as claimed in claim 1, wherein the $R^4$ alkyl chain has 15 carbons.

3. A composition of matter comprising the sophorolipids and sophorolipid analogs of claim 1, wherein the sophorolipids and sophorolipid analogs are used as antimicrobial agents, as antifungal agents, as biopesticides, as drugs to treat HIV, as drugs septic shock, as drugs cancer, as drugs asthma, as drugs dermatological conditions, as spermicidal agents, as anti-inflammatory drugs, as ingredients in cosmetics, and as building blocks for monomers and polymers and self-assembled templates for further chemical elaboration.

\* \* \* \* \*